United States Patent
Wilzbach et al.

(10) Patent No.: US 10,488,036 B2
(45) Date of Patent: Nov. 26, 2019

(54) SYSTEMS AND METHODS FOR ILLUMINATING AN OBJECT FIELD DURING A PROCESSING PROCESS OF A LIGHT CURING PLASTIC

(71) Applicant: Carl Zeiss Meditec AG, Jena (DE)

(72) Inventors: Marco Wilzbach, Stuttgart (DE); Tomas Lang, Essen (DE); Christian Schwedes, Aalen (DE); Carl Kübler, Aalen (DE); Peter Gangler, Herdecke (DE)

(73) Assignee: CARL ZEISS MEDITEC AG, Jena (DE)

( * ) Notice: Subject to any disclaimer, the term of this patent is extended or adjusted under 35 U.S.C. 154(b) by 399 days.

(21) Appl. No.: 15/592,626

(22) Filed: May 11, 2017

(65) Prior Publication Data
US 2017/0328556 A1   Nov. 16, 2017

(30) Foreign Application Priority Data
May 11, 2016   (DE) .......................... 10 2016 005 806

(51) Int. Cl.
  *F21V 33/00* (2006.01)
  *G02B 5/20* (2006.01)
  (Continued)

(52) U.S. Cl.
  CPC ............ *F21V 33/0068* (2013.01); *A61C 5/00* (2013.01); *A61C 19/003* (2013.01);
  (Continued)

(58) Field of Classification Search
  CPC .......... G02B 5/201; G02B 5/22; G02B 5/223; G02B 5/20; G02B 1/04; G02B 5/003;
  (Continued)

(56) References Cited

U.S. PATENT DOCUMENTS

2004/0076921 A1   4/2004 Gofman et al.
2009/0091913 A1   4/2009 Li et al.
(Continued)

FOREIGN PATENT DOCUMENTS

DE      603 05 832 T2   10/2006
DE   10 2006 004 232 B4   10/2007
(Continued)

OTHER PUBLICATIONS

German Office Action, with translation thereof, for corresponding DE application No. 10 2016 005 806.4 dated Jan. 3, 2017.

*Primary Examiner* — Collin X Beatty
*Assistant Examiner* — Grant A Gagnon
(74) *Attorney, Agent, or Firm* — Nixon Peabody LLP; Jeffrey L. Costellia

(57) ABSTRACT

Presented herein is an optical filter system for visible light, which has a first average transmittance $T_1$ between a limit wavelength $\lambda_G$ and a wavelength of 700 nm and a second average transmittance $T_2$ between a wavelength of 380 nm and the limit wavelength $\lambda_G$. In this case: 410 nm$<\lambda_G<$520 nm and 0.05

$$< \frac{T_1}{T_2} < 0.60.$$

17 Claims, 10 Drawing Sheets

(51) Int. Cl.
   *A61C 5/00* (2017.01)
   *A61C 13/15* (2006.01)
   *A61K 6/00* (2006.01)
   *F21V 14/08* (2006.01)
   *G02B 26/00* (2006.01)
   *F21W 131/202* (2006.01)
   *G02B 7/00* (2006.01)

(52) U.S. Cl.
   CPC ............ *A61K 6/0052* (2013.01); *F21V 14/08* (2013.01); *G02B 5/20* (2013.01); *G02B 5/208* (2013.01); *G02B 26/007* (2013.01); *F21W 2131/202* (2013.01); *G02B 7/006* (2013.01)

(58) Field of Classification Search
   CPC .. G02B 5/208; G02B 5/285; G02B 2207/101; G02B 5/286; G02B 1/041; G02B 5/008; G02B 5/085; G02B 5/205; G02B 5/206; G02B 5/23; G02B 21/16; G02B 26/008; G02B 27/2214; G02B 3/0031; G02B 5/26; G02B 13/0085; G02B 1/005; G02B 21/06; G02B 2207/113; G02B 3/00; G02B 3/005; G02B 5/1809; G02B 5/24; G02B 1/007; G02B 1/043; G02B 1/06; G02B 1/105; G02B 1/113; G02B 1/115; G02B 1/118; G02B 1/12; G02B 1/14; G02B 1/16; G02B 2207/121; G02B 2207/123; G02B 26/001; G02B 26/004; G02B 26/02; G02B 26/023; G02B 27/00; G02B 27/0018; G02B 27/1006; G02B 27/2207; G02B 27/2228; G02B 27/26; G02B 27/30; G02B 3/0062; G02B 3/0087; G02B 5/005; G02B 5/0215; G02B 5/0242; G02B 5/0278; G02B 5/0816; G02B 5/0825; G02B 5/0841; G02B 5/204; G02B 5/207; G02B 5/284; G02B 5/289; G02B 5/3016; G02B 5/3058; F21V 9/08; F21V 9/30; F21V 13/08; F21V 17/04; F21V 9/00; F21V 9/06; F21V 9/12; F21V 9/40
   USPC ........................................................ 359/885
   See application file for complete search history.

(56) References Cited

U.S. PATENT DOCUMENTS

| | | |
|---|---|---|
| 2010/0110538 A1 | 5/2010 | Steffen et al. |
| 2012/0300294 A1 | 11/2012 | Jess et al. |

FOREIGN PATENT DOCUMENTS

| | | |
|---|---|---|
| DE | 10 2010 033 825 A1 | 2/2012 |
| DE | 10 2013 013 426 A1 | 2/2015 |
| EP | 2 649 930 B1 | 6/2015 |
| WO | WO 2013/135516 A1 | 9/2013 |

SYSTEMS AND METHODS FOR ILLUMINATING AN OBJECT FIELD DURING A PROCESSING PROCESS OF A LIGHT CURING PLASTIC

PRIORITY

This application claims priority according to 35 U.S.C. § 119 to German patent application No. 10 2016 005 806.4, filed on May 11, 2016, the disclosure of which is incorporated herein by reference.

SUMMARY

The invention relates to systems and to the use thereof for illuminating an object field during a processing process of a light curing plastic, in particular during processing of a light curing plastic, used in dental medicine, in the region of teeth.

In dental medicine, light curing plastic are used, for example, as filling material. The light curing plastic used here are special substances that are plastic in non-polymerized form and solid in polymerized form. Polymerization of the respective plastic is activated here by irradiating with light of corresponding wavelengths and, in the process, via activation of photoinitiators contained in the plastic. The respective wavelength ranges that are effective for exciting polymerization here predominantly lie in the short-wave range of the visible spectrum (between 380 nm and 520 nm).

During placing and processing of the light curing plastic in an object field, typically an illumination system is used that illuminates the object field, but is not intended to activate the polymerization of the light curing plastic. The light used for polymerization is typically radiated into the object field via a separate illumination system after processing of the plastic in order to polymerize and thus cure the plastic to be processed.

A known illumination system comprises a broadband light source and a filter system, wherein the filter system is arranged in a beam path between the broadband light source and the object field. The filter system then only allows transmission of light that substantially does not result in polymerization of the plastic. However, this results in the light that is provided for illuminating the object field having significant gaps in the visible spectrum that can be found primarily in the short-wave range of the visible spectrum. As a result, the object field can be perceived only under a distorted colour impression. In particular, differences in the white shades between teeth situated in the object field and a plastic to be processed appear significantly distorted, which is frequently perceived as a red shift and, among other things, makes matching the colour shade of the plastic to the colour of the teeth to be treated more difficult.

Accordingly, it is an object of the present invention to provide systems and methods for illuminating an object field during a processing process of a light curing plastic. During the processing process, a colour impression that is as undistorted as possible is to be made possible with a sufficiently high illuminance of the object field, and premature curing of the light curing plastic is to be avoided as far as possible, i.e. curing of the light curing plastic is delayed.

For achieving the object, an illumination system according to the invention comprises at least one light source and irradiates an object field with visible light that has only a low irradiance for short wavelengths and a high irradiance for long wavelengths.

According to embodiments of the invention, a filter system has a first average transmittance $T_1$ in a transmission range between a limit wavelength $\lambda_G$ and a wavelength of 700 nm and a second average transmittance $T_2$ in a dimming range between a wavelength of 380 nm and the limit wavelength $\lambda_G$. What applies here is that the limit wavelength $\lambda_G$ is between 410 nm and 520 nm and a quotient of the second average transmittance $T_2$ and the first average transmittance $T_1$ takes on a value between 0.05 and 0.60.

Here, the first average transmittance $T_1$ and the second average transmittance $T_2$ can be calculated as follows:

$$T_1 = (700\,\text{nm} - \lambda_G)^{-1} \cdot \int_{\lambda_G}^{700nm} T(\lambda) d\lambda$$

and $$T_2 = (\lambda_G - 380\,\text{nm})^{-1} \cdot \int_{380nm}^{\lambda_G} T(\lambda) d\lambda$$

wherein
$\lambda$ is the wavelength; and
$T(\lambda)$ is a wavelength-dependent transmittance of the filter system.

In contrast to traditional "orange filters", as they are known, a filter system of this type allows through at least a small portion of the short-wave light that results in weak curing of the light curing plastic. This small amount of transmitted short-wave light is selected to be so low that the curing of the light curing plastic that is effected by this light has no substantial influence on a processability of the plastic yet, but significantly improves the colour impression obtained on the object. It should be noted that the filter system is not limited to transmission filters by the wording "transmission range", but the filter system can likewise comprise reflection filters or the like. "Transmittance" is defined here by way of the proportion of light that is available in a beam path downstream of the corresponding filter system.

According to embodiments of the filter system, a first average transmittance $T_1$ is greater than 0.7, in particular greater than 0.8 or even greater than 0.9.

That means that the filter system as far as possible transmits light having wavelengths from the illumination range and thus allows for bright illumination of the object field.

According to embodiments of the filter system, a wavelength-dependent transmittance $T(\lambda)$ of the filter system over the dimming range deviates from the second average transmittance $T_2$, or over the illumination range from the first average transmittance $T_1$, by less than 0.15, in particular less than 0.1 or even less than 0.05, that is to say $|T(\lambda) - T_2| < 0.15$, 0.1 or 0.05, or $|T(\lambda) - T_1| < 0.15$, 0.1 or 0.05.

As a result, fluctuations of the wavelength-dependent transmittance in the dimming range or in the illumination range are kept very small, as a result of which it is possible to consider the wavelength-dependent transmittance in the dimming range or in the illumination range to be approximately constant for the sake of simplicity.

According to embodiments of the filter system, the transmission characteristic of the filter system has a transition range between a first wavelength $\lambda_1$ and a second wavelength $\lambda_2$. Here, the first wavelength $\lambda_1$ is between 380 nm and the limit wavelength $\lambda_G$, and the second wavelength $\lambda_2$ is between the limit wavelength $\lambda_G$ and 700 nm. A difference between the first wavelength $\lambda_1$ and the second wavelength $\lambda_2$ is greater than 20 nm. Within this transition range, deviations of the wavelength-dependent transmittance $T(\lambda)$ from a wavelength-dependent predetermined value $T_{soll}(\lambda)$ for the respective wavelength $\lambda$ are less than 0.15. Here, the wavelength-dependent predetermined value $T_{soll}(\lambda)$ is produced over an imaginary linear profile of the wavelength-dependent transmittance T(λ) in the transition range between the first wavelength $\lambda_1$ and the second wavelength $\lambda_2$. That means:

$$T_{soll}(\lambda) = \frac{T(\lambda_2) - T(\lambda_1)}{\lambda_2 - \lambda_1}(\lambda - \lambda_1) + T(\lambda_1)$$

and $|T(\lambda) - T_{soll}| < 0.15$ for all $\lambda$ with $\lambda_1 \leq \lambda \leq \lambda_2$.

As a result, the wavelength-dependent transmittance has in the transition range a ramp-type profile, wherein the wavelength-dependent transmittance at shorter wavelengths assumes smaller values than at greater wavelengths.

According to embodiments of the filter system, a difference between the second wavelength $\lambda_2$ and the first wavelength $\lambda_1$ is greater than 50 nm and in particular greater than 100 nm.

This gives a relatively broad transition range which can also comprise significant parts of the dimming range.

According to embodiments of the filter system, a quotient of the second average transmittance $T_2$ and the first average transmittance $T_1$ assumes values between 0.15 and 0.35.

According to embodiments of the filter system, a distance of a colour point of the filter system $\vec{R}$, which is produced via the wavelength-dependent transmittance of the filter system in the colour space of the CIE(1931) colour system $T(\vec{r})$, from the white point in the colour space of the CIE(1931) colour system $\vec{W}$ has a value of at most 0.3. In this case:

$$\frac{\int_S T(\vec{r}) \cdot \vec{r} \cdot dr}{\int_S T(\vec{r}) \cdot dr} = \vec{R};$$

and $|\vec{W} - \vec{R}| \leq 0.3;$ wherein $T(\vec{r})$ is the wavelength-dependent transmittance of the filter system in the colour space of the CIE(1931) colour system;

$\vec{r}$ are coordinates in the colour space of the CIE(1931) colour system; and S is the spectral colour line in the colour space of the CIE(1931) colour system.

Due to this special realization of the filter system, transmission of light is possible, when using a broadband light source, which allows for illumination of an object field that is relatively close to white light.

According to embodiments of the filter system, the distance of the colour point of the filter system $\vec{R}$ from the white point $\vec{W}$ in the colour space of the CIE(1931) colour system has a value of at most 0.2 and in particular a value of at most 0.1.

Embodiments of the invention provide an illumination system which comprises at least one light source for illuminating an object field and an optical filter system. The filter system can be of the type described previously. The filters of the filter system may be arranged here in an illumination beam path between the at least one light source and the object field.

It should be noted that the light source can be a light source that is as broadband as possible so as to permit setting of a profile of a wavelength-dependent spectral irradiance, with which the object field is finally irradiated, that is as free as possible by adaptation of the filter system.

According to embodiments of the illumination system, the light source comprises a xenon light source.

According to embodiments of the invention, an illumination system for illuminating an object field comprises at least one light source. The illumination system is here configured to radiate light in a plane at a distance of 30 cm from the illumination system, which light has a first average spectral irradiance $E_1$ in an illumination range between a limit wavelength $\lambda_G$ and a wavelength of 700 nm, and a second average spectral irradiance $E_2$ in a dimming range between a wavelength of 380 nm and the limit wavelength $\lambda_G$. What applies here is that the limit wavelength $\lambda_G$ is between 410 nm and 520 nm and a quotient of the second average spectral irradiance $E_2$ and the first average spectral irradiance takes on a value between 0.05 and 0.60.

It should be noted that in the case of the above-described dental application, the plane lies in an object field in which the light curing plastic is to be processed, and the distance between the plane and the illumination system is measured from the plane to a component of the illumination system that is nearest the plane.

Here, the first average spectral irradiance $E_1$ and the second average spectral irradiance $E_2$ can be determined, analogously to the first average transmittance $T_1$ and the second average transmittance $T_2$, by way of integration over the corresponding wavelength ranges.

Owing to an illumination system of this type, it is possible to illuminate the object field over the entire visible wavelength range from 380 nm to 700 nm with a sufficient brightness and at the same time a high colour rendering index (CRI), while curing of a light curing plastic in the object field is substantially not yet brought about due to the lower second average spectral irradiance in the dimming range. A treating person can consequently perceive the object field in a colour impression that is as undistorted as possible and at a sufficient brightness, and still have enough time to process the light curing plastic in the object field within a clinically relevant processing time.

The colour rendering index (CRI) is here ascertainable via spectral measurement of the illumination system and subsequent performance of numerical methods. These methods also represent a comparison of the measured spectrum to a corresponding reference spectrum so as to finally ascertain associated colour rendering indices in each case for specified test colours (cf. e.g. DIN 6169 14). The total colour rendering index (CRI) of the illumination system is then obtained via arithmetic averaging of the respectively ascertained colour rendering indices.

According to embodiments of the illumination system, a first irradiance $I_1 = E_1 \cdot (700 \text{ nm} - \lambda_G)$ which is radiated over the illumination range is greater than 10 W/m², preferably greater than 50 W/m² or more preferably greater than 150 W/m².

What is ensured hereby is that the illumination system radiates sufficient light into the plane over the illumination range to be able to allow for observation of the object field at sufficient brightness.

According to embodiments of the illumination system, the irradiation characteristic of the illumination system has a transition range between a third wavelength $\lambda_3$ and a fourth wavelength $\lambda_4$. Here, the third wavelength $\lambda_3$ is between 380 nm and the limit wavelength $\lambda_G$, and the fourth wavelength $\lambda_4$ is between the limit wavelength $\lambda_G$ and 700 nm. A difference between the third wavelength $\lambda_3$ and the fourth wavelength $\lambda_4$ is greater than 20 nm. Within this transition range, deviations of the wavelength-dependent spectral irradiance $E(\lambda)$ from a wavelength-dependent predetermined value $E_{soll}(\lambda)$ for the respective wavelength $\lambda$ are less than 0.15 W/m² nm. Here, the wavelength-dependent predetermined value $E_{soll}(\lambda)$ for the respective irradiance results by way of a fiction of a linear profile of the wavelength-dependent spectral irradiance $E(\lambda)$ in the transition range between the third wavelength $\lambda_3$ and the fourth wavelength $\lambda_4$. That means:

$$E_{soll}(\lambda) = \frac{E(\lambda_4) - E(\lambda_3)}{\lambda_4 - \lambda_3}(\lambda - \lambda_3) + E(\lambda_3)$$

and $$|E(\lambda) - E_{soll}| < 0.15 \frac{W}{m^2 nm} \text{ for all } \lambda \text{ with } \lambda_3 \leq \lambda \leq \lambda_4.$$

As a consequence, the wavelength-dependent spectral irradiance $E(\lambda)$, with which the plane is irradiated by the illumination system, has a ramp-type profile in the transition range, wherein the wavelength-dependent spectral irradiance at shorter wavelengths has smaller values than at greater wavelengths.

According to embodiments of the illumination system, the difference between the fourth wavelength $\lambda_4$ and the third wavelength $\lambda_3$ is greater than 50 nm and in particular greater than 100 nm.

This gives a relatively broad transition range which can also comprise significant parts of the dimming range.

According to embodiments of the illumination system, the quotient of the second average spectral irradiance $E_2$ and the first average spectral irradiance $E_1$ has a value between 0.15 and 0.35.

According to embodiments of the illumination system, a distance of the colour point $\vec{R}$ in the colour space of the CIE(1931) colour system that is determined by the wavelength-dependent spectral irradiance $E(\vec{r})$, which is radiated into the plane by the illumination system, from the white point $\vec{W}$ in the colour space of the CIE(1931) colour system has a value of at most 0.3. Here, the colour point $\vec{R}$ for the spectral irradiance can be ascertained analogously to the colour point for the transmittance by corresponding integration and subsequent normalization.

Due to this special configuration of the wavelength-dependent spectral irradiance, illumination is ensured that illuminates the object field as colour-neutrally as possible and thus allows for a colour impression at the object field that is as undistorted as possible.

According to embodiments of the illumination system, the distance of the colour point $\vec{R}$ that is determined by the wavelength-dependent spectral irradiance $E(\vec{r})$ from the white point $\vec{W}$ in the colour space of the CIE(1931) colour system has a value of at most 0.2 and in particular a value of at most 0.1.

According to embodiments of the illumination system, the illumination system comprises a plurality of light sources, the emission spectra of which differ from one another. Here, first light sources whose greatest part of the respective emission spectrum is in the dimming range and not in the illumination range in one operating mode radiate onto the plane with an irradiance that is at most 20% of the irradiance with which the plane is irradiated by way of second light sources whose greatest part of the respective emission spectrum is in the illumination range and not in the dimming range.

This means in effect, that the first light sources are dimmed with respect to the second light sources so as to obtain the irradiation characteristic according to the invention in the plane and thus at the object field.

According to embodiments of the illumination system, an irradiance $I_2$ with which the plane is irradiated at a distance of 30 cm from the illumination system over the wavelengths of the dimming range is less than 6 W/m². In this case:

$$I_2 = \int_{380nm}^{\lambda_G} E(\lambda) \cdot d\lambda;$$

wherein
$\lambda$ is the wavelength; and
$E(\lambda)$ is the wavelength-dependent spectral irradiance with which the plane is irradiated by the illumination system.

What is ensured hereby is that a curing process of a light curing plastic located in the plane precedes only very slowly, which offers sufficient time for processing the light curing plastic before the light curing plastic exhibits substantial signs of curing.

According to embodiments of the illumination system, the illumination system furthermore has a controller that is configured to set the illumination system into two different operating modes. In this case, the irradiance $I_2$ with which the plane is irradiated in a first operating mode with the distance of 30 cm from the illumination system over the wavelengths of the dimming range is less than 15 W/m², and in particular less than 10 W/m² or even less than 6 W/m². The irradiance $I_2$ with which the plane is irradiated in a second operating mode with the distance of 30 cm from the illumination system over the dimming range is greater than 15 W/m², and in particular greater than 30 W/m² or even greater than 50 W/m².

It is thus possible during use of the illumination system in the first operating mode to obtain illumination of the object field according to the invention and to thus be able to observe during the processing the light curing plastic at sufficient brightness and a relatively high colour rendering index with sufficient time for processing. If the processing of the light curing plastic is finally terminated, or brighter illumination of the object field becomes necessary, the illumination system can be set into the second operating mode via the controller. However, the light curing plastic is now excited to polymerization and thus curing by way of the highly irradiant light from the short-wave wavelength range (dimming range). The illumination system consequently has a first operating mode for illuminating during processing of a light curing plastic, and a second operating mode for normal-light illumination, which renders an additional illumination system for normal-light illumination unnecessary.

According to embodiments, the illumination system comprises an actuator that is configured to arrange filters of the illumination system in an illumination beam path between the light source and the plane for the first operating mode, and to remove the filters of the illumination system from the beam path between the light source and the plane for the second operating mode, wherein the controller is configured to control the actuator.

This embodiment is an example of a realization of switchability of the operating modes in an illumination system, which comprises a broadband light source and a correspondingly adapted filter system.

According to embodiments of the invention, the illumination system comprises a plurality of light sources, the emission spectra of which differ from one another. Here, first light sources whose greatest part of the respective emission spectrum is in the dimming range and not in the illumination range are dimmed during operation in the first operating mode by at least 80% as compared to operation in the second operating mode, wherein the controller is configured to control dimming of the first light sources.

This embodiment is an example of a realization of switchability of the operating modes in an illumination system, which comprises a plurality of light sources of various types and substantially no filters.

According to embodiments of the illumination system, the illumination system is configured such that an illuminance $E_V$ of at least 10 kLux is achieved by the illumination system in the plane with the distance of 30 cm from the illumination system. In this case:

$$E_V = 250 \frac{\text{lm}}{W} \cdot \int_{380\text{nm}}^{700\text{nm}} E(\lambda) \cdot d\lambda$$

wherein
λ is a wavelength; and
E(λ) is the wavelength-dependent spectral irradiance with which the plane is irradiated by the illumination system.

With this configuration, sufficiently bright illumination of the object field is ensured.

According to embodiments of the invention, the illumination system is used for illuminating an object field during processing of a light curing plastic in the object field.

According to exemplary embodiments, the light curing plastic here comprises Lucirin TPO, phenyl propanedione, Ivocerin and/or camphorquinone.

Here, said photoinitiators represent the photoinitiators that are currently used with the highest frequency in dentistry.

According to exemplary embodiments, the light curing plastic is attached to a tooth.

According to exemplary embodiments, an effective irradiance $I_{2;\text{eff}}$ which is radiated over the dimming range and results in curing of the light curing plastic, is less than 6 W/m². In this case:

$$I_{2;\text{eff}} = \int_{380\text{nm}}^{\lambda_G} A(\lambda) \cdot E(\lambda) \cdot d\lambda$$

wherein
λ is the wavelength;
E(λ) is the wavelength-dependent spectral irradiance with which the object field is irradiated by the illumination system; and
A(λ) is a wavelength-dependent absorbance of the light curing plastic located in the object field.

It is thus possible to prevent a light curing plastic located in the object field from curing too quickly and to have sufficient time for processing the light curing plastic. The absorption curves relating to the best known plastics materials used in dentistry are shown in the attached figures.

According to exemplary embodiments, an effective dose $D_{2;\text{eff}}$ that is radiated onto the light curing plastic over the dimming range during illumination of the object field is less than 360 J/m². In this case:

$$D_{2;\text{eff}} = t \cdot I_{2;\text{eff}} = \int_{380\text{nm}}^{\lambda_G} A(\lambda) \cdot E(\lambda) \cdot d\lambda$$

wherein
λ is the wavelength;
t is a period of the illumination of the object field with the illumination system;
E(λ) is the wavelength-dependent spectral irradiance with which the object field is irradiated by the illumination system; and
A(λ) is the wavelength-dependent absorbance of a light curing plastic located in the object field.

That means that the object field and thus the light curing plastic is illuminated with the illumination system only until substantial curing of the plastic is not yet noticeable.

According to exemplary embodiments, a colour rendering index obtained during the use of the illumination system in the object field is greater than 60, preferably greater than 70, with further preference greater than 80 and most preferably greater than 90.

According to exemplary embodiments, illuminance $E_V$ that is obtained during the use of the illumination system in the object field is greater than 10 kLux. In this case:

$$E_V = 250 \frac{\text{lm}}{W} \cdot \int_{380\text{nm}}^{700\text{nm}} E(\lambda) \cdot d\lambda$$

wherein
λ is the wavelength; and
E(λ) is the wavelength-dependent spectral irradiance with which the object field is irradiated by the illumination system.

Consequently, sufficiently bright illumination of the object field is ensured.

According to exemplary embodiments, the limit wavelength $\lambda_G$ is selected such that it is at a wavelength for which the wavelength-dependent spectral irradiance E(λ) is exactly central between the first average spectral irradiance $E_1$ and the second average spectral irradiance $E_2$, in other words: $E(\lambda_G) = (E_1 + E_2)/0.5$.

This ensures that the limit wavelength determines the transition between the dimming range and the illumination range and is not selected randomly.

According to embodiments of the invention, an observation system comprises a light source for illuminating an object field, a filter system according to the invention, and an imaging optical unit for imaging the object field, wherein the optical filter system is arranged in a beam path between the light source and the object field.

According to embodiments of the invention, an observation system comprises an illumination system according to the invention and an imaging optical unit for imaging the object field.

BRIEF DESCRIPTION OF THE DRAWINGS

Exemplary embodiments of the invention are explained in more detail below on the basis of figures.

Figure 1:
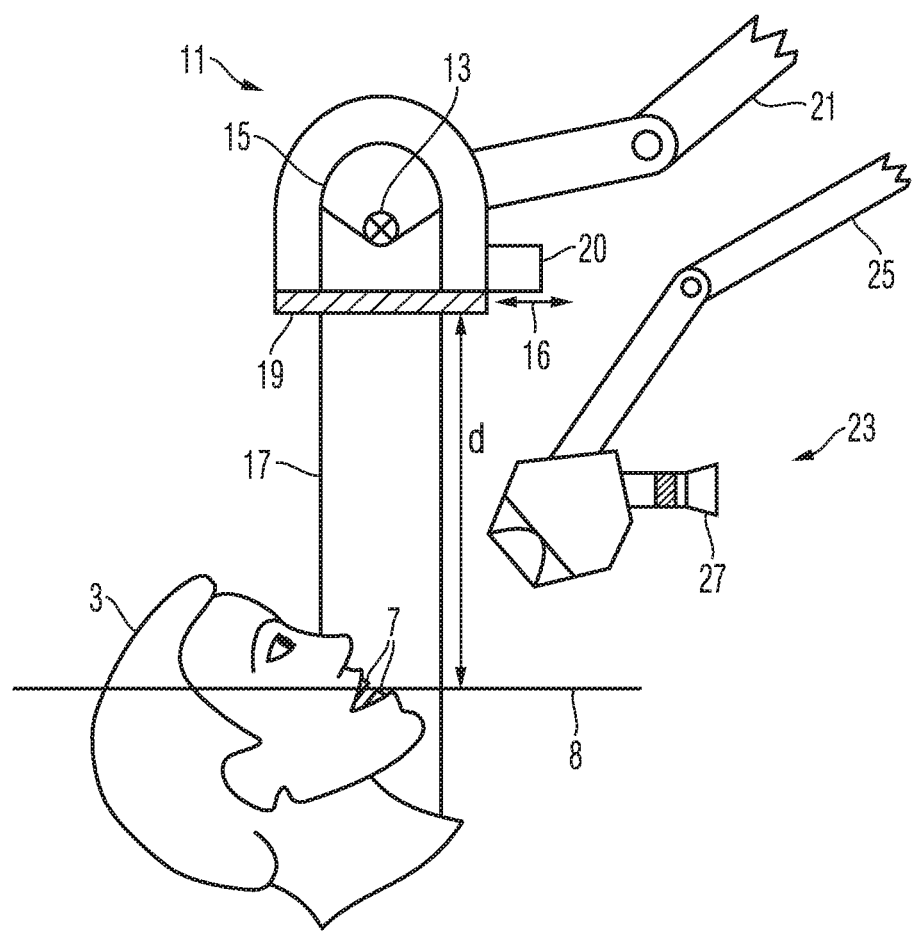
FIG. 1 shows an exemplary configuration of an optical observation system in accordance with one embodiment of the invention.

The present disclosure is susceptible to various modifications and alternative forms, and some representative embodiments have been shown by way of example in the drawings and will be described in detail herein. It should be understood, however, that the inventive aspects are not limited to the particular forms illustrated in the drawings. Rather, the disclosure is to cover all modifications, equivalents, and alternatives falling within the spirit and scope of the disclosure as defined by the appended claims.

DETAILED DESCRIPTION OF ILLUSTRATED EXAMPLES

FIG. 1 shows an exemplary embodiment of the invention as an observation system. The exemplary observation system here comprises an illumination system 11 and an imaging optical unit 23. The illumination system is directed at teeth 7 in the head 3 of a patient, on which a light curing plastic for processing is placed. An object plane 8, in which the teeth 7 of the patient are located, has a distance d along a beam path 17 from a component of the illumination system 11 that is located closest to the object plane 8, here configured as a transmission filter 19, that in the present example is 30 cm. A light source 13 emits light which is shaped into a light beam 17 via a parabolic reflection mirror 15 and directed onto the object plane 8. In the present example, the light source is in the form of a xenon light source, wherein other light sources having sufficiently strong emission in the visible spectrum can also be used as the light source. A transmission filter 19 is arrangeable, with the aid of an actuator 20, in a beam path from the light source 13 to the object field 8, which is indicated by way of a double-headed arrow 16, to filter the light coming from the light source 13 before it is incident on the object field 8. In order to facilitate handling of the illumination system 11, the illumination system 11 is attached to a stand 21 that is fixed to the ceiling or the floor of the treatment room. The illumination system 11 can be brought into a desired orientation with respect to the object field via the stand and be ultimately fixed therein. The observation system has the imaging optical unit 23 for observing the object field. A treating person can then observe the object field 8 through an eyepiece 27 of the imaging optical unit 23. Similarly to the illumination system 11, the imaging optical unit 23 is also fixed to the ceiling or the floor of the treatment room using a stand 25.

In the example shown, the imaging optical unit 23 and the observation system 11 are housed in separate housings, which are supported by separate stands. However, it is also possible for the imaging optical unit and the observation system to be housed in a common housing, which is supported on a single stand.

So as now to be able to observe the object field 8 with sufficient brightness and colour fidelity, without bringing about premature curing of the light curing plastic, the illumination system 11 could be configured as follows.

Figure 2:
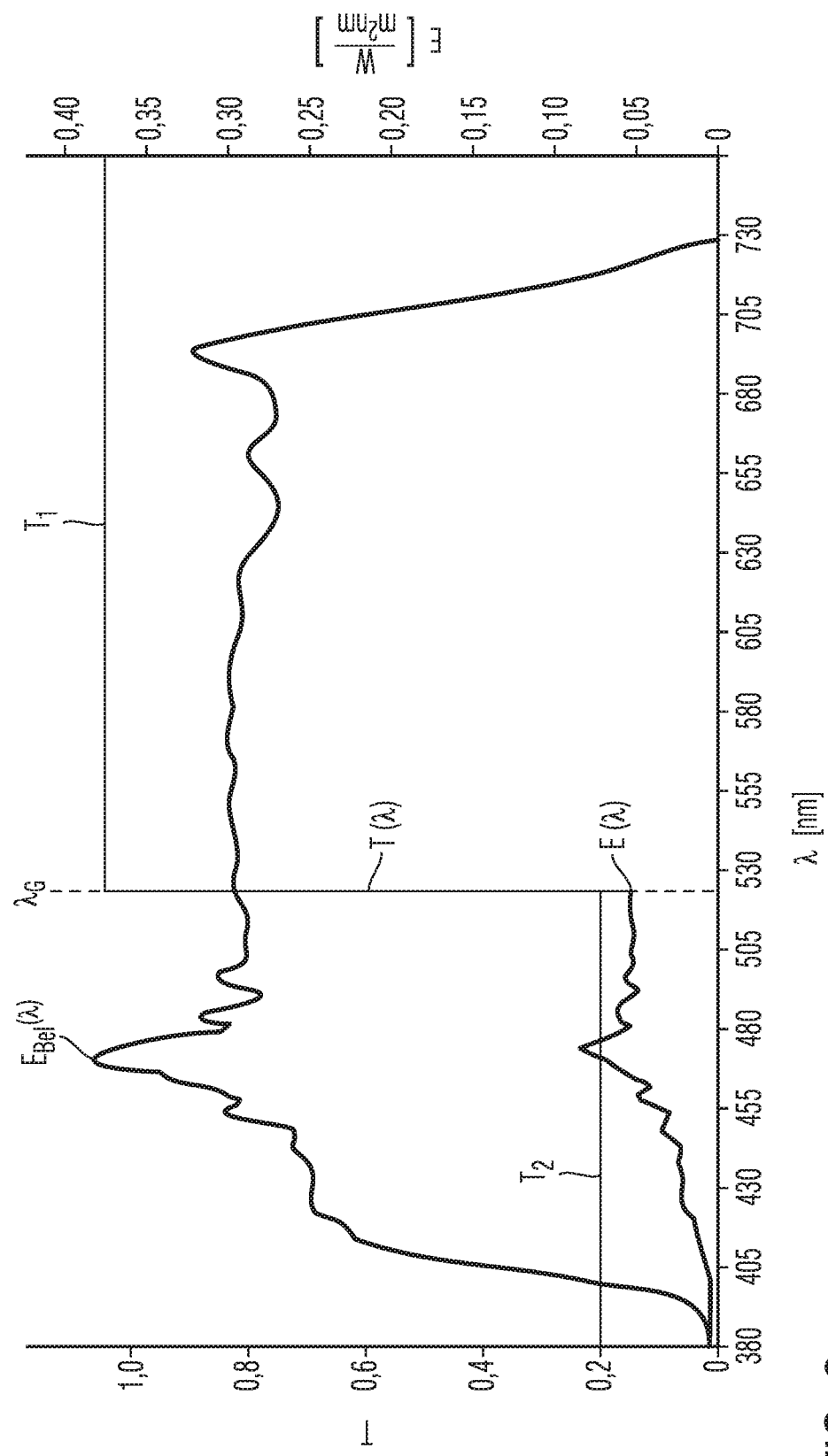
FIG. 2 shows graphs that represent an emission spectrum of a broadband light source and a transmission characteristic of a filter system.
Figure 3A:
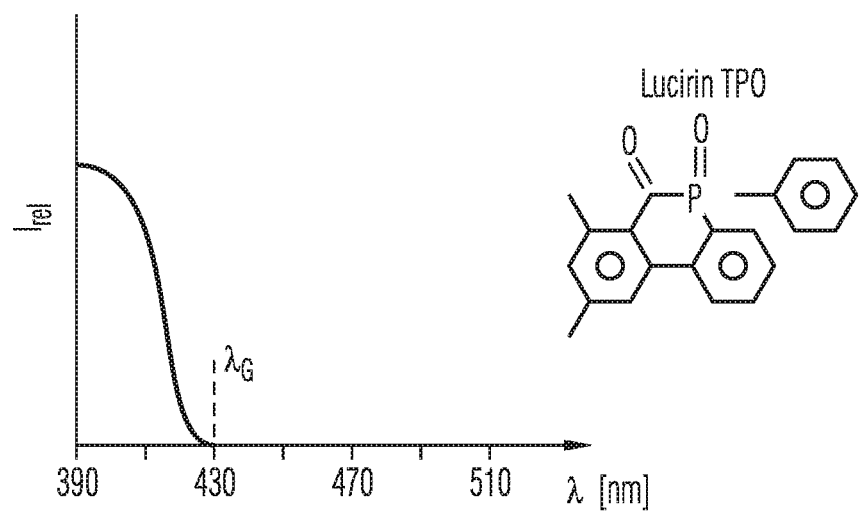
FIGS. 3A to 3D show absorption curves of frequently used photoinitiators.
Figure 3B:
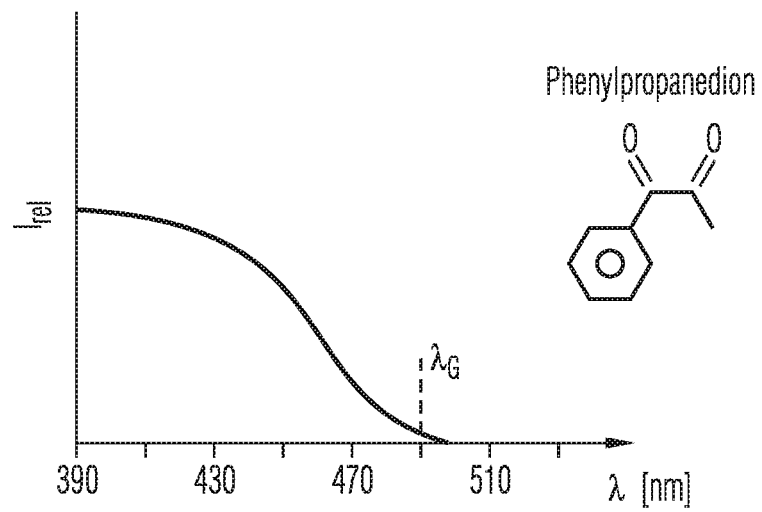
Figure 3C:
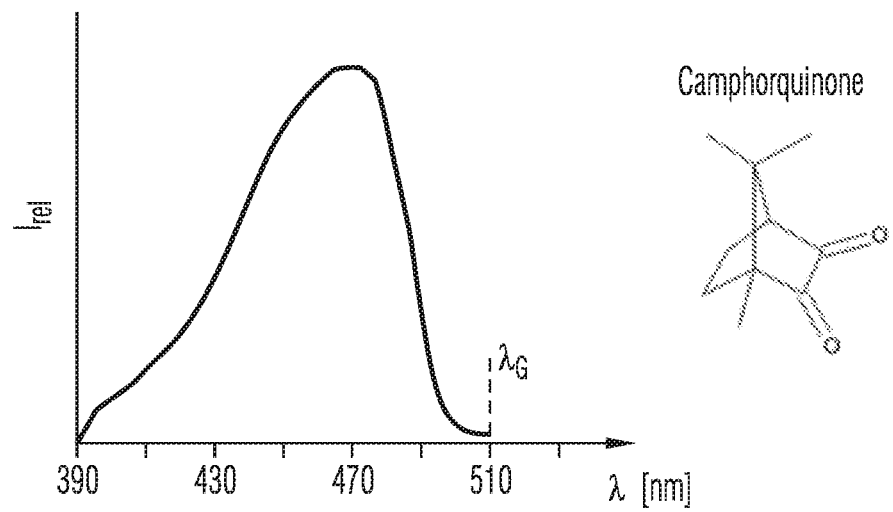
Figure 3D:
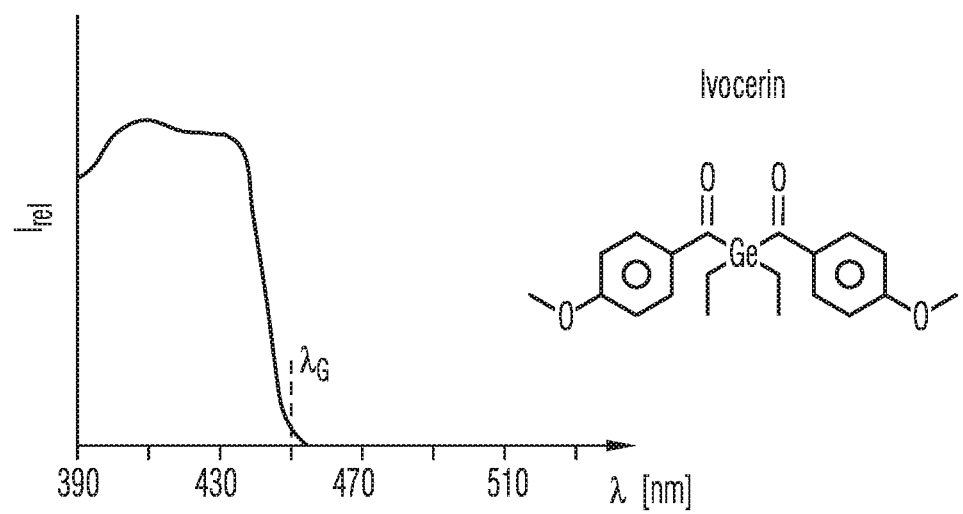

FIG. 2 shows an exemplary emission characteristic $E_{Bel}(\lambda)$ of the light source 13 and an exemplary transmission characteristic $T(\lambda)$ of the transmission filter 19 in the form of graphs, which show a spectral irradiance E in $$\frac{W}{m^2 nm}$$

and respectively, a transmittance T (dimensionless) as a function of the wavelength $\lambda$ in nm. Also shown is a spectral irradiance $E(\lambda)$ with which the object field would ultimately be irradiated by the exemplary illumination system 11.

The emission characteristic $E_{Bel}(\lambda)$ has an approximately constant value for the wavelengths from 420 nm to 705 nm. Under direct illumination of the object field by way of the light source, this would, due to a significant irradiation with light of short wavelengths, which generally results in curing of a light curing plastic, result in fast curing of the light curing plastic. In order to prevent this, a wavelength-dependent transmittance $T(\lambda)$ of the transmission filter 19 has a first transmittance $T_1$ in a transmission range between a limit wavelength $\lambda_G$ and a wavelength of 700 nm, and a second transmittance $T_2$ in a dimming range between 380 nm and the limit wavelength $\lambda_G$. Here, the limit wavelength $\lambda_G$ is selected such that light having wavelengths below the limit wavelength $\lambda_G$ causes curing of the light curing plastic, and light having wavelengths above the limit wavelength $\lambda_G$ does not cause curing of the light curing plastic. In addition, the second transmittance $T_2$ having an exemplary value of 0.2 is significantly smaller than the first transmittance $T_1$, which has an exemplary value of 1.0, and is still significantly greater than zero. If the transmission filter 19 is now, as described, arranged in the beam path between the light source 13 and the object plane 8, short-wave light having wavelengths from the dimming range of the transmission filter reaches the object plane only with a significantly reduced spectral irradiance, while light having wavelengths from the illumination range of the transmission filter still has a very high irradiance in the object field. Light having a spectral irradiance illustrated in graph $E(\lambda)$ thus still arrives in the object plane. On the one hand, due to the comparatively low irradiance $E(\lambda)$ in the dimming range (as compared to the illumination range) that is received in the object field, no significant curing of the light curing plastic is brought about yet. On the other hand, the comparatively high irradiance $E(\lambda)$ in the illumination range allows for a high illuminance in the object field, which is necessary for detailed observation of the object field. A distortion of a colour impression on the object that would be caused by the comparatively high irradiance in the illumination range is here compensated for as much as possible by the remaining irradiance $E(\lambda)$ that is radiated over the dimming range (cf. $T_2$=0.2), which allows a largely colour-neutral illumination of the object field.

It is thus possible for the object field and thus the light curing plastic to be illuminated in the object field with sufficient brightness and colour neutrality, without bringing about substantial curing of the light curing plastic.

In order to achieve the best possible illumination, the limit wavelength λG must be adapted as well as possible to the respective light curing plastic to be processed in the object field.

FIGS. 3A to 3D show absorption curves of a number of photoinitiators that are common in dentistry and are used in light curing plastics for activating polymerization in the form of graphs that indicate a relative intensity $I_{rel}$ (dimensionless) as a function of the wavelength λ in nm. While a suitable limit wavelength λG for Lucirin TPO (cf. FIG. 3A) could be, for example, 430 nm, a suitable limit wavelength λG for phenyl propanedione (cf. FIG. 3B) could be approximately 490 nm, for camphorquinone (cf. FIG. 3C) approximately 510 nm and for Ivocerin (cf. FIG. 3D) approximately 450 nm.

Figure 4:
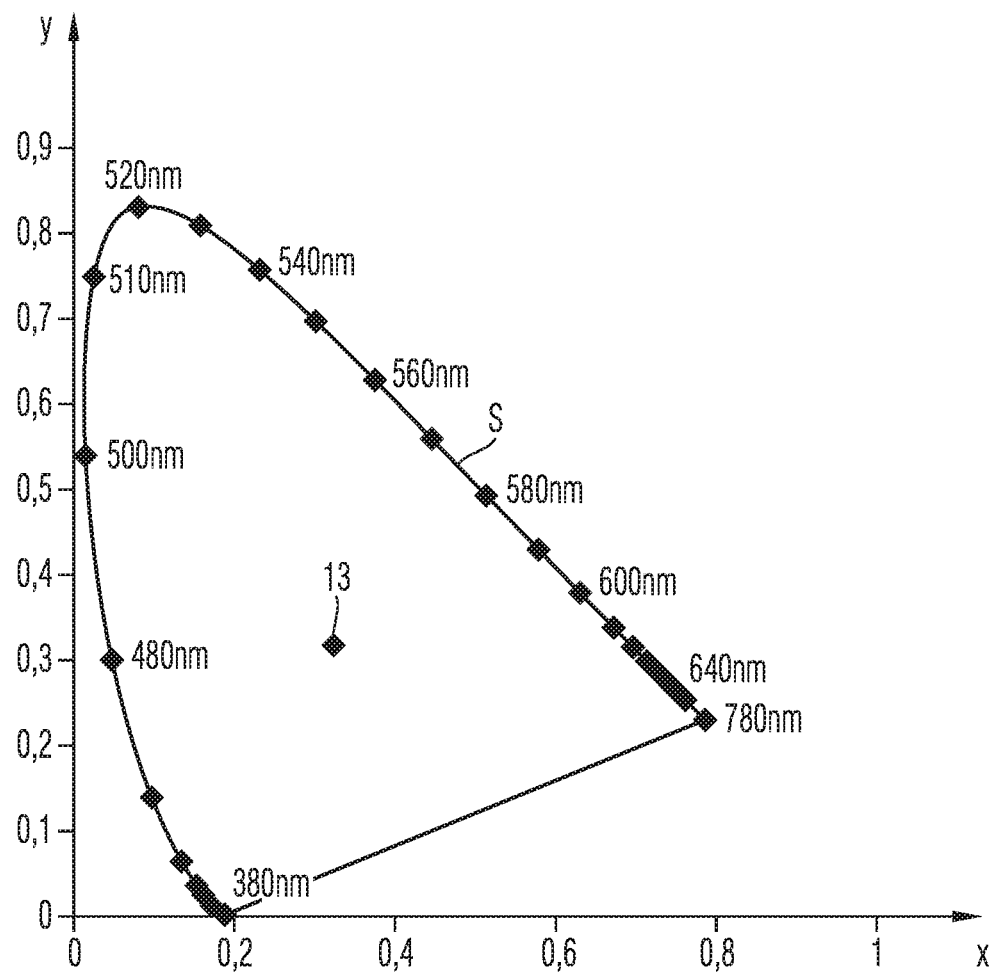
FIG. 4 shows a representation of the colour space of the CIE(1931) colour system.

With the colour space of the CIE(1931) colour system, FIG. 4 shows an alternative to the CRI for assessing colour neutrality (or colour rendering) of a system. In order to be able to perform the corresponding assessment, an x-coordinate and a y-coordinate of a colour point $\vec{R}$ of an illumination system (or of a filter system) in the colour space of the CIE(1931) colour system must be ascertained by way of integration and subsequent normalization of a wavelength-dependent spectral irradiance (or a transmittance) along a spectral colour line S in the colour space of the CIE(1931) colour system:

$$\frac{\int_S E(\vec{r}) \cdot \vec{r} \cdot dr}{\int_S E(\vec{r}) \cdot dr} = \vec{R};$$

wherein $E(\vec{r})$ is the wavelength-dependent spectral irradiance $E(\lambda)$ in the colour space of the CIE(1931) colour system, with which an object plane is irradiated by the illumination system;

$\vec{r}$ are coordinates in the colour space of the CIE(1931) colour system; and S is the spectral colour line in the colour space of the CIE(1931) colour system.

A distance of the colour point $\vec{R}$ that is thus obtained from the white point $\vec{W}$ in the colour space of the CIE(1931) colour system then shows how colour neutral the illumination system (or the filter system) is. If the distance is less than 0.3 or less than 0.2 or even less than 0.1, a significant colour neutrality of the illumination system (or of the filter system) can be assumed.

In order to meet specific requirements of average transmittances $T_1$ and $T_2$ of filter systems, wavelength-dependent transmittances T(λ) can be formed in various manners. Similar is true here also for wavelength-dependent spectral irradiances of illumination systems FIGS. 5A and 5B and FIGS. 6A and 6B show transmission curves T(λ) of examples of filter systems in the form of graphs, which show a transmittance T (dimensionless) as a function of the wavelength λ in nm. It should be noted that the term "transmission curve" is not a limitation on a component-related realization of the filter system, and the filter system can also easily comprise reflection filters or the like.

Figure 5A:
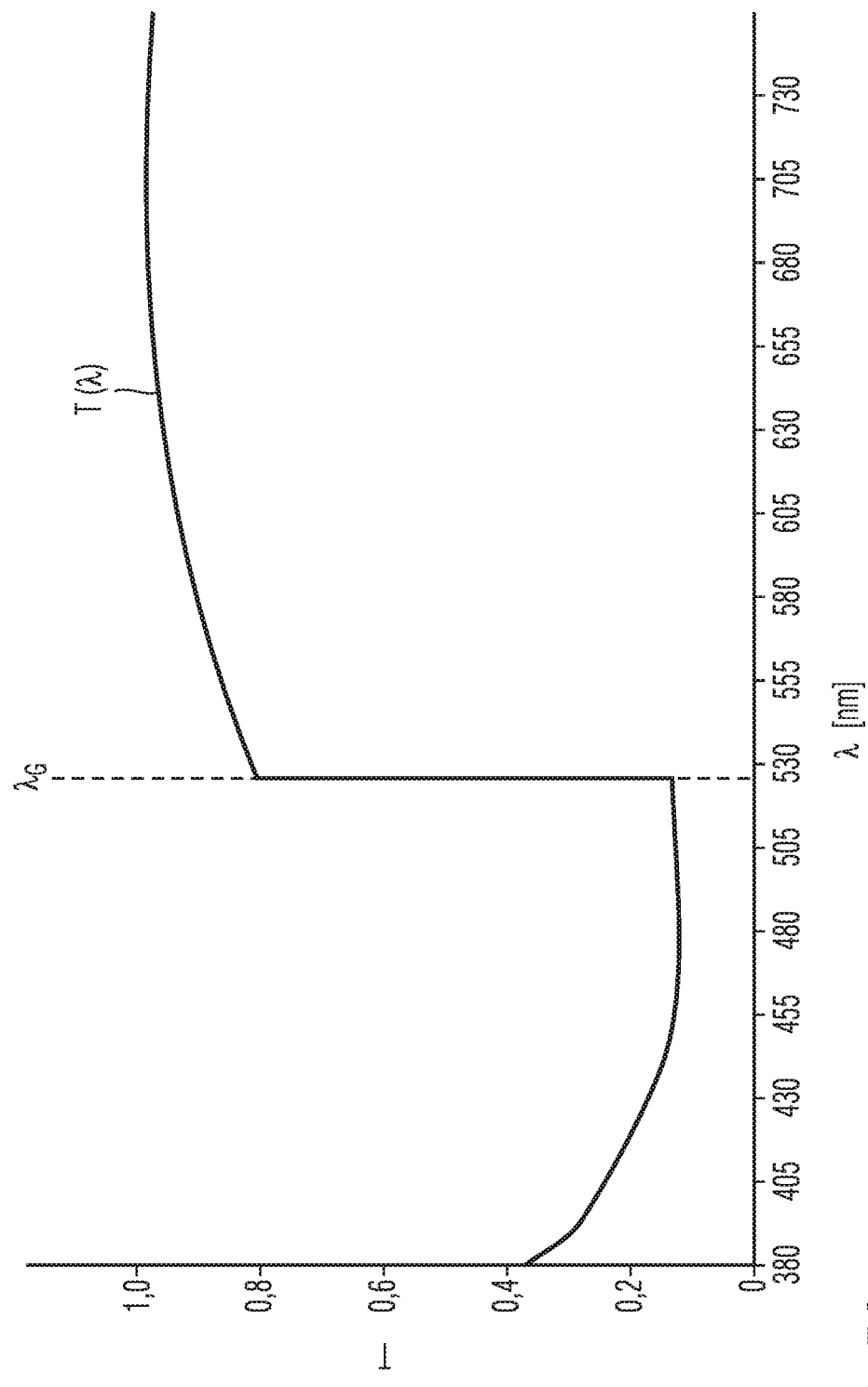
FIGS. 5A and 5B show exemplary transmission characteristics of filter systems in accordance with embodiments of the invention.

The wavelength-dependent transmittance T(λ) from FIG. 5A starts at a wavelength of 380 nm with a value of approximately 0.35 and then approaches a significantly lower value of approximately 0.14 with increasing wavelength. At the limit wavelength λG, a jump of the wavelength-dependent transmittance T(λ) to a significantly higher value of approximately 0.78 occurs. Starting from this higher value, the wavelength-dependent transmittance T(λ) continues to increase with greater wavelengths and finally approaches a still higher value of approximately 0.95. Transmission filters of this type could, for example, be advantageous when working with light curing plastics having camphorquinone (cf. FIG. 3C), because at wavelengths of 380 nm to 430 nm for which camphorquinone has only a lower absorbance, an increased (as compared to the wavelengths of 430 nm to 490 nm) spectral irradiance is radiated into the object field and thus colour rendering in the object field can be significantly improved, without bringing about significant curing of the light curing plastic in the object field.

Figure 5B:
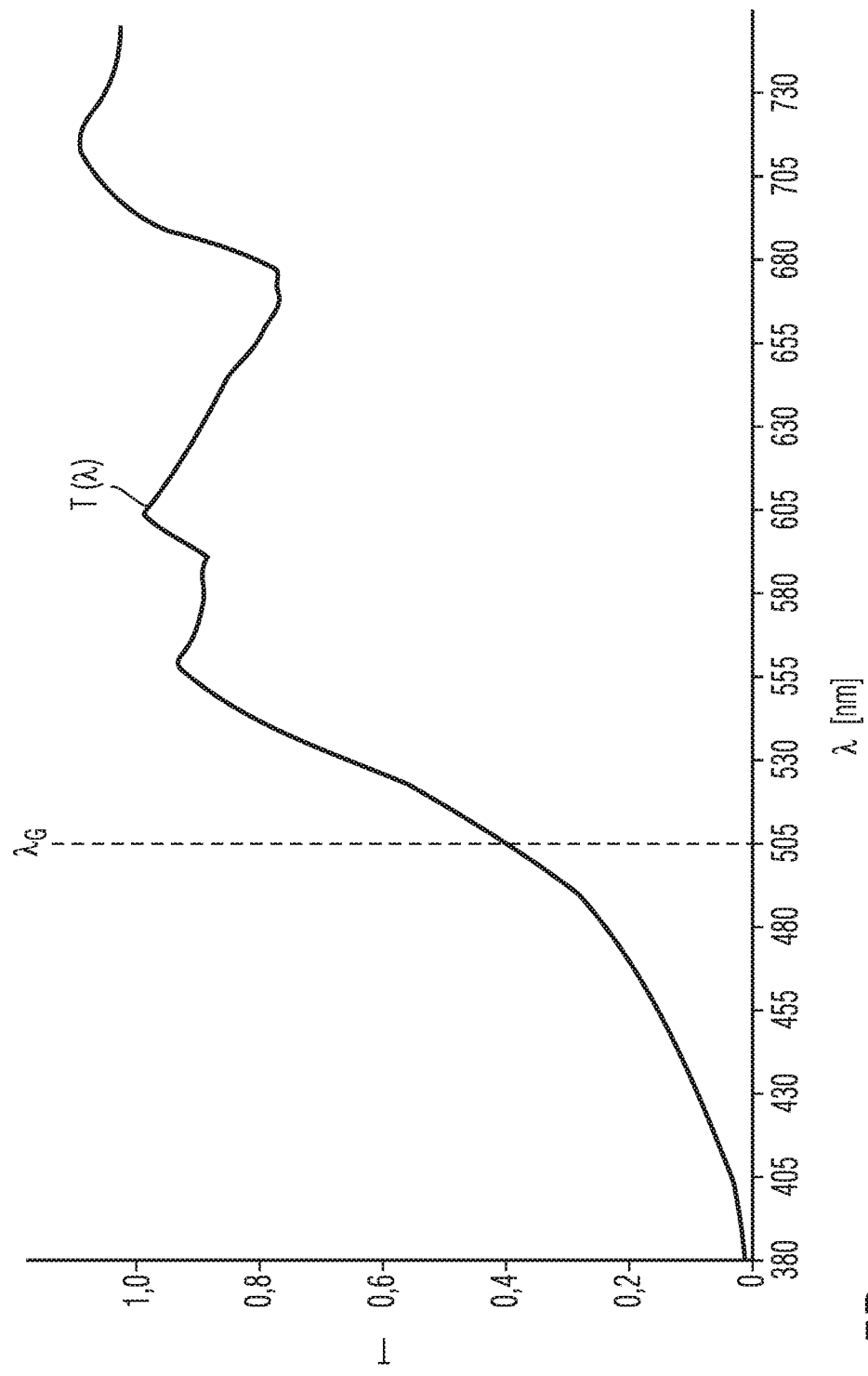

FIG. 5B shows a further wavelength-dependent transmittance T(λ), wherein here the transmittance T(λ) continuously increases with the wavelength up to a wavelength of approximately 550 nm. At wavelengths of greater than 555 nm, significant fluctuations of the wavelength-dependent transmittance T(λ) occur. Such a profile is conceivable in filter systems, in which an exact profile of the transmittance T(λ) in the short-wave range up to, for example, 555 nm is very important, and a profile of the transmittance T(λ) in the long-wave range of greater than, for example, 555 nm does not need to be as well defined.

Figure 6A:
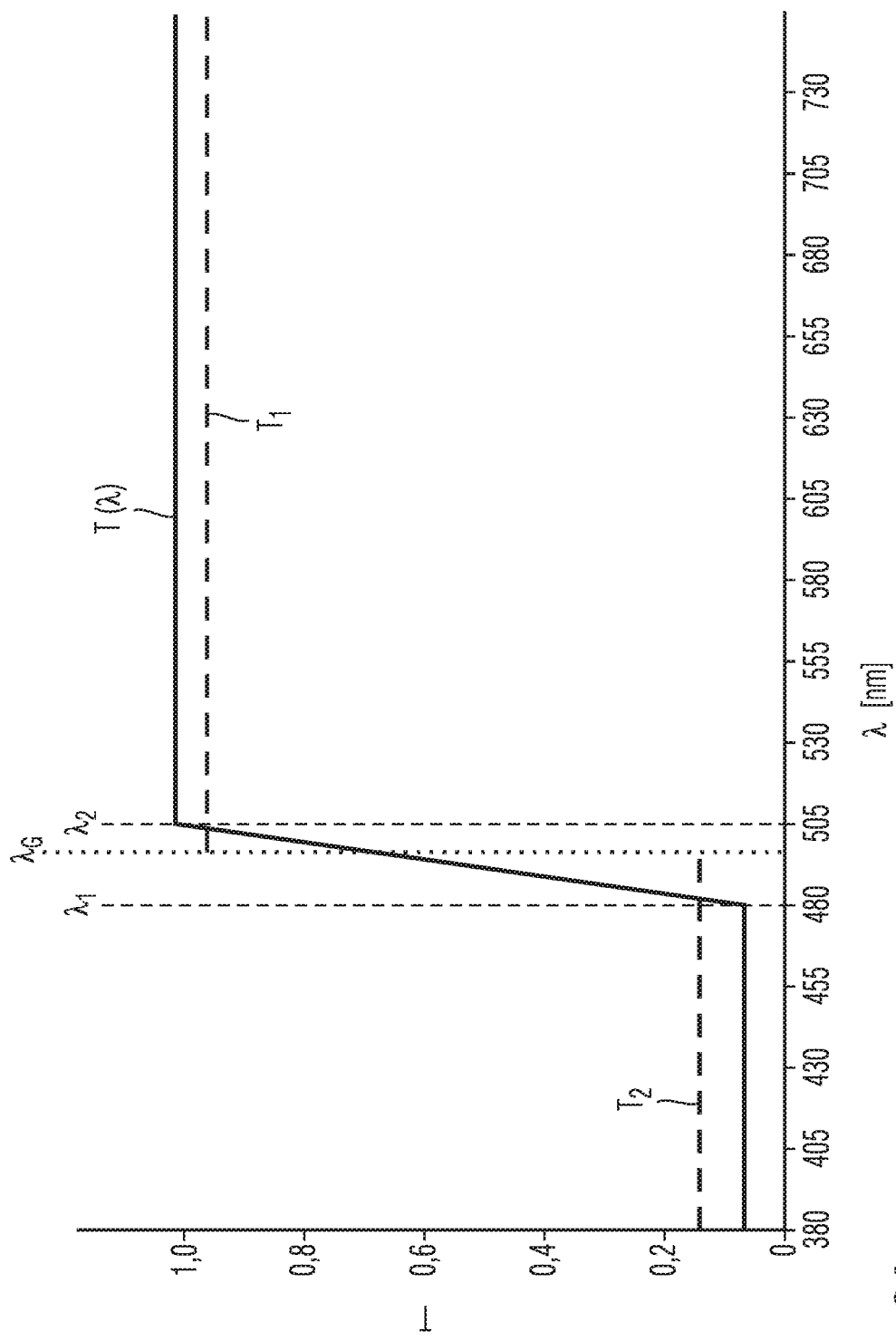
FIGS. 6A and 6B show exemplary transmission characteristics of filter systems in accordance with embodiments of the invention.

FIG. 6A shows a further exemplary, highly idealized wavelength-dependent transmittance T(λ), which has a transition range between a first wavelength $\lambda_1$ and a second wavelength $\lambda_2$. It should be noted that the limit wavelength $\lambda_G$ that separates a transmission range (above the limit wavelength) from a dimming range (below the limit wavelength) lies between the first wavelength $\lambda_1$ and the second wavelength $\lambda_2$. A corresponding filter system here has a first average transmittance $T_1$ over the transmission range, which is significantly greater than a second average transmittance $T_2$ of the dimming range. In the transition range, the wavelength-dependent transmittance T(λ) is very steep and is linear with respect to the wavelength, as a result of which a relatively abrupt and well-defined transition from the dimming range to the transmission range is achieved.

Figure 6B:
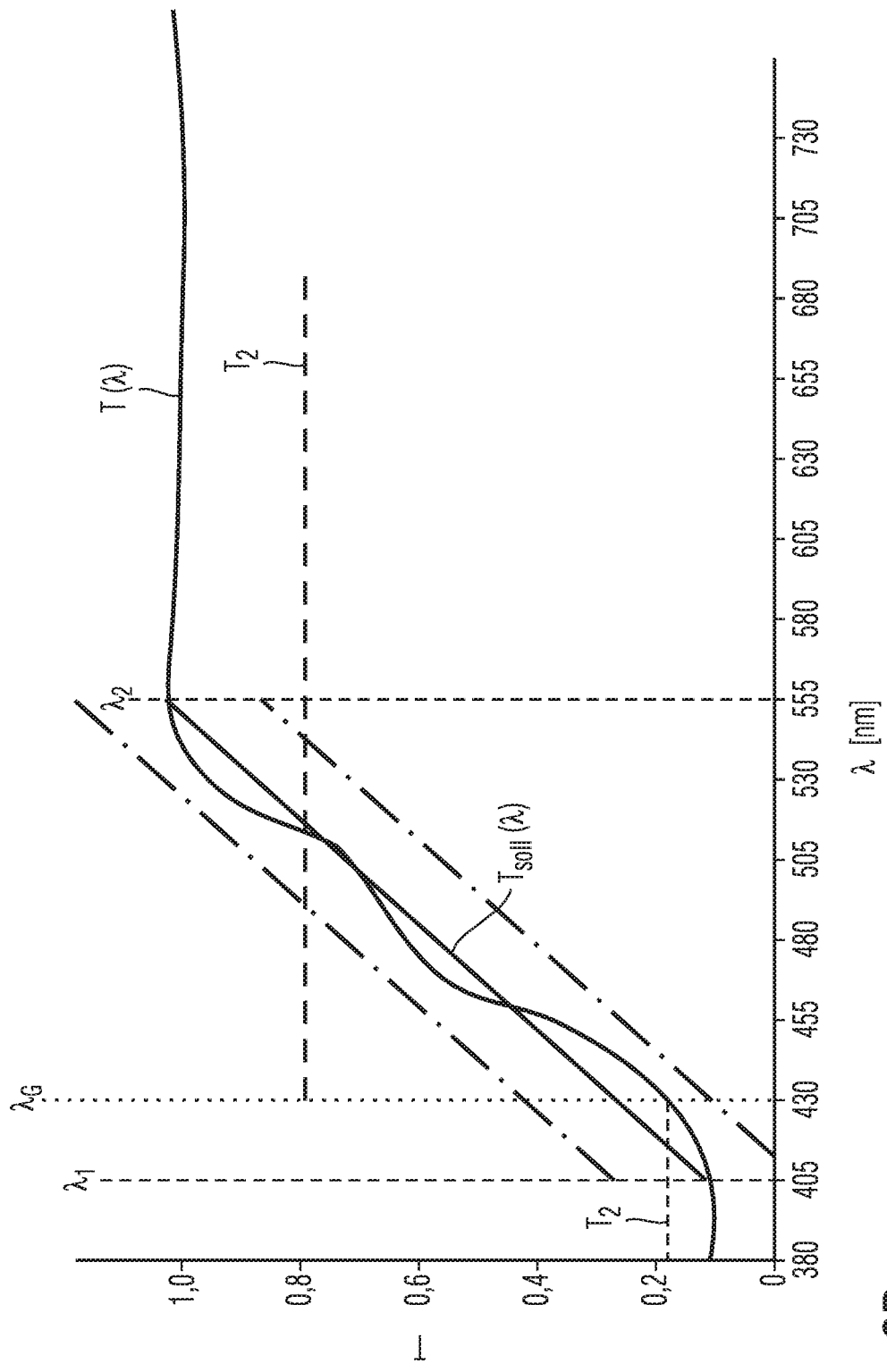

FIG. 6B shows a further wavelength-dependent transmittance T(λ), wherein here the two wavelengths $\lambda_1$ and $\lambda_2$ are significantly further apart than in FIG. 6A. This results in a relatively broad transition range. In the transition range between the first wavelength $\lambda_1$ and the second wavelength $\lambda_2$, the wavelength-dependent transmittance T(λ) shown here does not follow exactly a linear profile, which is indicated by the graph $T_{soll}(\lambda)$, wherein:

$$T_{soll}(\lambda) = \frac{T(\lambda_2) - T(\lambda_1)}{\lambda_2 - \lambda_1}(\lambda - \lambda_1) + T(\lambda_1).$$

However, all values T(λ) lie within a narrow corridor around the linear graph $T_{soll}(\Delta)$:

$|T(\lambda) - T_{soll}(\lambda)| < 0.15$ for all λ with $\lambda_1 \leq \lambda \leq \lambda_2$;

(indicated by way of the dot-dash line), as a result of which the wavelength-dependent transmittance T(λ) over the transition range can be approximated, for the sake of simplicity, as being linearly increasing with the wavelength λ. It is also important to note here that the limit wavelength $\lambda_G$ is between the first limit wavelength $\lambda_1$ and the second limit wavelength $\lambda_2$ and separates a transmission range with a first average transmittance $T_1 \approx 0.8$ from a dimming range with a second average transmittance $T_2 \approx 0.18$, wherein the first average transmittance $T_1$ is considerably greater than the second average transmittance $T_2$, and the second average transmittance $T_2$ is still considerably greater than zero.

In addition to the exemplary transmission curves shown, many other transmission curves are conceivable which still fall within the spirit of the invention.

Figure 7:
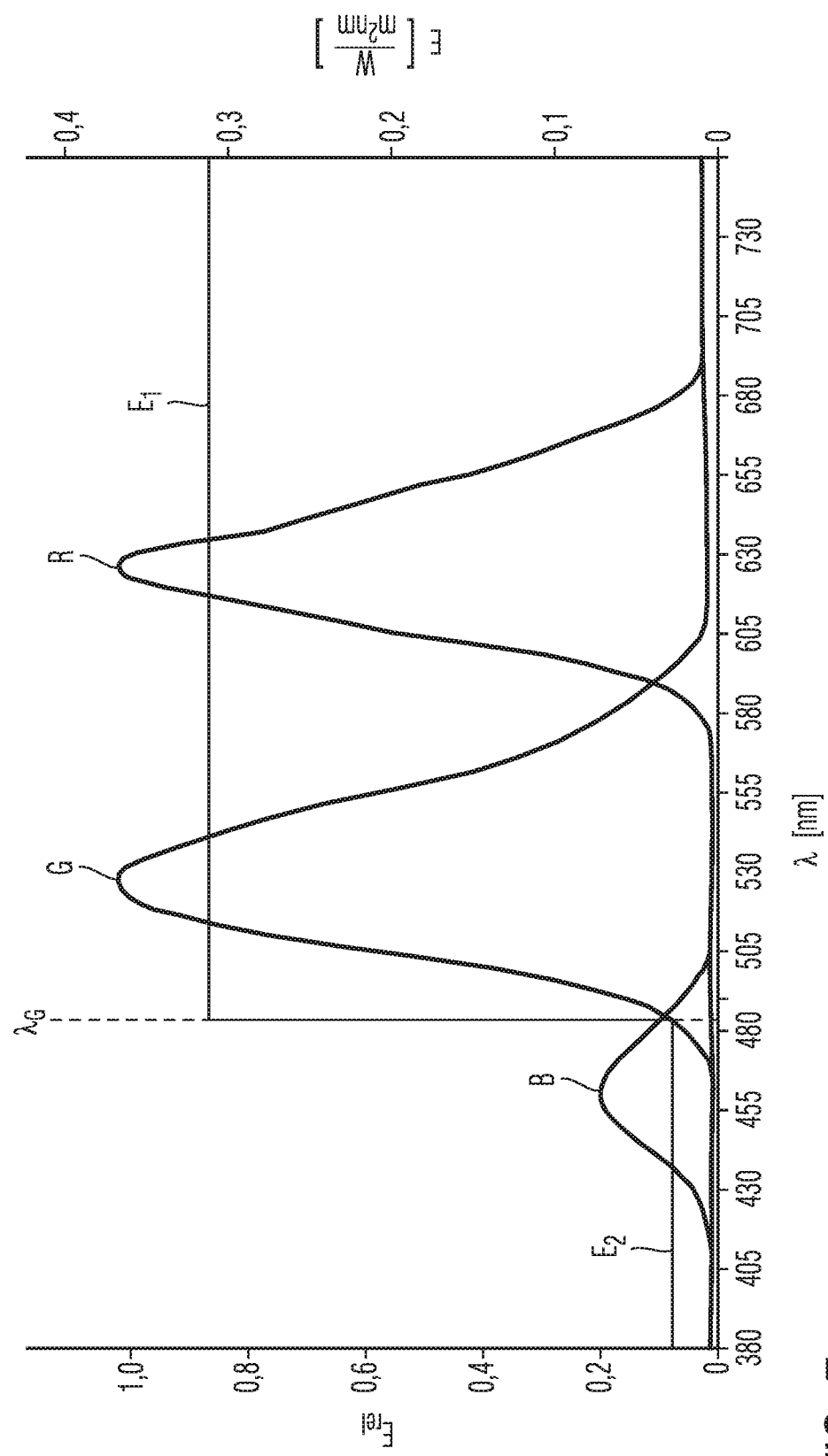
FIG. 7 shows graphs that represent the emission spectra of different light sources and a transmission characteristic of a filter system.

FIG. 7 shows emission curves (R, G, B) of three different light sources and average spectral irradiances (E1 und E2) of an illumination system according to a further embodiment of the invention in the form of graphs, which indicate a relative spectral irradiance $E_{rel}$ (dimensionless) or a spectral irradiance E in $$\frac{W}{m^2 nm}$$

as a function of the wavelength λ in nm. A first light source is a red LED, the relative spectral irradiance of which is indicated by the graph R. A second light source is a green LED, the relative spectral irradiance of which is indicated by the graph G. The red LED and the green LED radiate with approximately the same maximum spectral irradiance so as to be able to provide in each case approximately the same irradiance in an object field. A third light source is a blue LED, the relative spectral irradiance of which is indicated by the graph B. A maximum spectral irradiance of the blue LED is here significantly reduced as compared to the spectral irradiances of the red and the green LEDs, which can be achieved, for example, by dimming the blue LED. As a combination of the three different light sources, the illumination system (consisting of the three LEDs) has in an illumination range from a limit wavelength λG to a wavelength of 700 nm a first average spectral irradiance E1. Here, this first average spectral irradiance $E_1$ is provided primarily from light from the red and the green LED. Over a dimming range from 380 nm to the limit wavelength λG, a second average spectral irradiance E2 is obtained. It should be noted here that this second average spectral irradiance is provided substantially via light of the blue LED. The second average spectral irradiance $E_2$ is significantly smaller than the first average spectral irradiance $E_1$, as a result of which curing of a light curing plastic is delayed, while a bright and colour neutral illumination of an object field is made possible. The limit wavelength $\lambda_6$ is here, as already described above, adapted to a light curing plastic that is to be illuminated.

Such an illumination system, which consists of three or more different and separately controllable light sources, has significant advantages. First, the spectral irradiances radiated by the red LED and the green LED into an object field can be chosen to be so high that the object field is illuminated with a sufficiently high illuminance. In addition, the blue LED can be dimmed, independently of these two other LEDs, to an extent such that curing of the light curing plastic that is to be illuminated is delayed, and additionally a total colour impression that is similar to white light is brought about in the object field. It is not necessary here to develop a specific filter system or adapt it to individual light curing plastics, since adapting a respective light curing plastic takes place merely by way of adapting the irradiances of the individual light sources (R, G, B). Such an illumination system can have a plurality of operating modes, wherein the blue LED radiates, for example, with the same maximum irradiance onto the object field as the red and the green LED in one operating mode, while it is dimmed in another operating mode by at least 80% in order to radiate onto the object field with an irradiance of less than 20% of the irradiance with which the red and the green LED radiate onto the object field.

The invention claimed is:

1. Optical filter system for visible light, which in a wavelength range of 380 nm to 700 nm has the following transmission characteristic: a transmission range between a limit wavelength $\lambda_G$ and a wavelength of 700 nm, wherein the transmission range between the limit wavelength $\lambda_G$ and the wavelength of 700 nm has a first average transmittance $T_1$; and a dimming range between a wavelength of 380 nm and the limit wavelength $\lambda_G$, wherein the dimming range between the wavelength of 380 nm and the limit wavelength $\lambda_G$ has a second average transmittance $T_2$; where: $410 < \lambda_G < 520$ nm, and $0.05 < T_2/T_1 < 0.60$.

2. Optical filter system according to claim 1, wherein the transmission characteristic of the filter system has a transition range that extends between a first wavelength $\lambda_1$ and a second wavelength $\lambda_2$, wherein:
380 nm$<\lambda_1<\lambda_G<\lambda_2<$700 nm;
$\lambda_2-\lambda_1>20$ nm $$T_{soll}(\lambda) = \frac{T(\lambda_2) - T(\lambda_1)}{\lambda_2 - \lambda_1}(\lambda - \lambda_1) + T(\lambda_1)$$

and $|T(\lambda) - T_{soll}| < 0.15$ for all λ with $\lambda_1 \le \lambda \le \lambda_2$;

wherein
T(λ) is a wavelength-dependent transmittance of the filter system.

3. Optical filter system according to claim 1, wherein:

$$\frac{\int_S T(\vec{r}) \cdot \vec{r} \cdot dr}{\int_S T(\vec{r}) \cdot dr} = \vec{R}$$

and $|\vec{W} - \vec{R}| \le 0.3;$ wherein
T(r) is a wavelength-dependent transmittance of the filter system in the colour space of the CIE(1931) colour system;
$\vec{r}$ are coordinates in the colour space of the CIE(1931) colour system;
S is the spectral colour line in the colour space of the CIE(1931) colour system; and
$\vec{W}$ is the white point in the colour space of the CIE(1931) colour system.

4. Optical observation system, comprising:
an imaging optical unit for imaging an object field;
a light source for illuminating the object field; and
an optical filter system according to claim 1, wherein the optical filter system is arranged in a beam path between the light source and the object field.

5. Optical illumination system for illuminating an object field with visible light in a wavelength range of 380 nm to 700 nm, wherein the illumination system comprises at least one light source and has the following irradiation characteristic in a plane at a distance of 30 cm from the illumination system:

an illumination range
between a limit wavelength $\lambda_G$
and a wavelength of 700 nm,
wherein over the illumination range a first average spectral irradiance $E_1$ is radiated by the illumination system onto the plane;
a dimming range
between a wavelength of 380 nm
and the limit wavelength $\lambda_G$,
wherein over the dimming range a second average spectral irradiance $E_2$ is radiated by the illumination system onto the plane;
where:

$$410 < \lambda_G < 520\text{nm}$$

and $$0.05 < \frac{E_2}{E_1} < 0.60.$$

6. Optical illumination system according to claim 5, wherein:

$$I_1 = E_1 \cdot (700\text{nm} - \lambda_G)$$

and $$I_1 > 10 \frac{W}{m^2},$$

and in particular $$I_1 > 50 \frac{W}{m^2}$$

or $$I_1 > 150 \frac{W}{m^2}.$$

7. Optical illumination system according to claim 5, wherein the irradiation characteristic of the illumination system has a transition range that extends between a third wavelength $\lambda_3$ and a fourth wavelength $\lambda_4$, wherein:
380 nm<$\lambda_3$<$\lambda_G$<$\lambda_4$<700 nm;
$\lambda_4 - \lambda_3 > 20$ nm $$E_{soll}(\lambda) = \frac{E(\lambda_4) - E(\lambda_3)}{\lambda_4 - \lambda_3}(\lambda - \lambda_3) + E(\lambda_3)$$

and $$|E(\lambda) - E_{soll}| < 0.15 \frac{W}{m^2 \text{nm}} \text{ for all } \lambda \text{ with } \lambda_3 \leq \lambda \leq \lambda_4;$$

$E(\lambda)$ is a wavelength-dependent spectral irradiance with which the plane is irradiated by the illumination system.

8. Optical illumination system according to claim 5, wherein $$\frac{\int_S E(\vec{r}) \cdot \vec{r} \cdot dr}{\int_S E(\vec{r}) \cdot dr} = \vec{R}$$

and $$|\vec{W} - \vec{R}| \leq 0.3;$$

wherein $E(\vec{r})$ is a wavelength-dependent spectral irradiance in the colour space of the CIE(1931) colour system, with which the plane is irradiated by the illumination system;

$\vec{r}$ are coordinates in the colour space of the CIE(1931) colour system;

S is the spectral colour line in the colour space of the CIE(1931) colour system; and $\vec{W}$ is the white point in the colour space of the CIE(1931) colour system.

9. Optical illumination system according to claim 5, wherein the illumination system comprises a plurality of light sources whose emission spectra differ from one another, wherein first light sources whose greatest part of the respective emission spectrum is in the dimming range and not in the illumination range in one operating mode radiate onto the plane with an irradiance that is at most 20 percent of the irradiance with which the plane is irradiated by way of second light sources whose greatest part of the respective emission spectrum is in the illumination range and not in the dimming range.

10. Optical illumination system according to claim 5, wherein the illumination system is configured such that in a plane at a distance of 30 cm from the illumination system:

$$I_2 = \int_{380\text{nm}}^{\lambda_G} E(\lambda) \cdot d\lambda$$

and $$I_2 < 15 \frac{W}{m^2},$$

and in particular $$I_2 < 10 \frac{W}{m^2} \text{ or } I_2 < 6 \frac{W}{m^2},$$

wherein $\lambda$ is a wavelength; and $E(\lambda)$ is a wavelength-dependent spectral irradiance with which the plane is irradiated by the illumination system.

11. Optical illumination system according to claim 5, furthermore comprising a controller that is configured to set the illumination system into two different operating modes, wherein in a first operating mode in the plane at the distance of 30 cm from the illumination system:

$$I_2 < 15 \frac{W}{m^2},$$

and in particular $$I_2 < 10 \frac{W}{m^2} \text{ or } I_2 < 6 \frac{W}{m^2},$$

and in a second operating mode in the plane at the distance of 30 cm from the illumination system:

$$I_2 > 15 \frac{W}{m^2},$$

and in particular $$I_2 > 30 \frac{W}{m^2} \text{ or } I_2 > 50 \frac{W}{m^2}.$$

12. Optical illumination system according to claim 11, further comprising an actuator that is configured to arrange filters of the illumination system in an illumination beam path between the light source and the plane during the first operating mode, and to remove the filters of the illumination system from the beam path between the light source and the plane during the second operating mode, wherein the controller is configured to control the actuator.

13. Optical illumination system according to claim 11, wherein the illumination system comprises a plurality of light sources whose emission spectra differ from one another, wherein irradiances from first light sources whose greatest part of the respective emission spectrum is in the dimming range and not in the illumination range are reduced by at least 80 percent during operation in the first operating mode as compared to operation in the second operating mode, wherein the controller is configured to control the reduction in the respective irradiances of the first light sources.

14. Use of the optical illumination system according to claim 5 for illuminating an object field during processing of a light curing plastic in the object field, wherein the light curing plastic comprises in particular Lucirin TPO and/or phenyl propanedione and/or Ivocerin and/or camphorquinone, and wherein the light curing plastic is attached in particular to a tooth.

15. Use according to claim 14, wherein:

$$I_{2;eff} = \int_{380nm}^{\lambda_G} A(\lambda) \cdot E(\lambda) \cdot d\lambda$$

and $$I_{2,eff} < 6 \frac{W}{m^2};$$

wherein
$\lambda$ is a wavelength;
$E(\lambda)$ is a wavelength-dependent spectral irradiance with which the object field is irradiated by the illumination system; and
$A(\lambda)$ is a wavelength-dependent absorbance of a light curing plastic located in the object field.

16. Use according to claim 14, wherein:

$$D_{2;eff} = t \cdot I_{2;eff} = \int_{380nm}^{\lambda_G} A(\lambda) \cdot E(\lambda) \cdot d\lambda$$

and $$D_{2,eff} < 360 \frac{J}{m^2};$$

wherein
$\lambda$ is a wavelength;
t is a period of the illumination of the object field with the illumination system;
$E(\lambda)$ is a wavelength-dependent spectral irradiance with which the object field is irradiated by the illumination system; and
$A(\lambda)$ is a wavelength-dependent absorbance of a light curing plastic located in the object field.

17. Optical observation system, comprising:
an imaging optical unit for imaging an object field;
a light source for illuminating the object field; and
an optical illumination system according to claim 5.

* * * * *

UNITED STATES PATENT AND TRADEMARK OFFICE
CERTIFICATE OF CORRECTION

PATENT NO. : 10,488,036 B2
APPLICATION NO. : 15/592626
DATED : November 26, 2019
INVENTOR(S) : Wilzbach et al.

Page 1 of 1

It is certified that error appears in the above-identified patent and that said Letters Patent is hereby corrected as shown below:

On the Title Page

Item (57) Abstract, last line:
"$0.05 < \frac{T_1}{T_2} < 0.60$" should read "$0.05 < \frac{T_2}{T_1} < 0.60$"

In the Specification

Column 12, Line 59:
"$T_{soll}(\Delta)$" should read "$T_{soll}(\lambda)$"

Column 13, Line 48:
"$\lambda_6$" should read "$\lambda_G$"

In the Claims

Column 14, Line 19:
"$410 < \lambda_G < 520$ nm" should read "$410$ nm $< \lambda_G < 520$ nm"

Column 15, Line 20:
"$410 < \lambda_G < 520$ nm" should read "$410$ nm $< \lambda_G < 520$ nm"

Column 18, Line 11:
"$I_{2,eff}$" should read "$I_{2;eff}$"

Column 18, Line 29:
"$D_{2,eff}$" should read "$D_{2;eff}$"

Signed and Sealed this
Thirteenth Day of October, 2020

Andrei Iancu
*Director of the United States Patent and Trademark Office*